United States Patent [19]

Hesse et al.

[11] 4,205,997

[45] * Jun. 3, 1980

[54] POWDERY PEARLESCENT PIGMENT COMPOSITIONS

[75] Inventors: Reiner Hesse; Hans Pratzer; Manfred Kieser; Gerhard Edler, all of Darmstadt, Fed. Rep. of Germany

[73] Assignee: Merck Patent Gesellschaft mit Beschrankter Haftung, Darmstadt, Fed. Rep. of Germany

[ * ] Notice: The portion of the term of this patent subsequent to Sep. 26, 1995, has been disclaimed.

[21] Appl. No.: 918,239

[22] Filed: Jun. 23, 1978

Related U.S. Application Data

[63] Continuation-in-part of Ser. No. 763,157, Jan. 27, 1977, Pat. No. 4,116,628.

[30] Foreign Application Priority Data

Jan. 29, 1976 [DE] Fed. Rep. of Germany ....... 2603211

[51] Int. Cl.$^2$ .............................................. C09C 1/00
[52] U.S. Cl. ............................. 106/308 Q; 106/291; 106/308 M; 106/308 N; 428/407
[58] Field of Search ............... 106/291, 308 Q, 308 N, 106/308 M; 428;407/; 424/64, 358

[56] References Cited

U.S. PATENT DOCUMENTS

| | | | |
|---|---|---|---|
| 2,332,220 | 11/1939 | Harshberger | 106/291 |
| 3,080,258 | 3/1963 | Davis | 106/308 M |
| 3,379,674 | 4/1968 | Jakob et al. | 106/291 |
| 3,492,253 | 1/1970 | Katz et al. | 106/308 N |
| 3,773,708 | 11/1973 | Takahashi et al. | 106/308 Q |
| 3,819,566 | 6/1974 | Pinsky et al. | 106/308 M |
| 3,897,586 | 7/1975 | Coker | 428/407 |
| 3,904,562 | 9/1975 | Hopfenberg et al. | 106/308 M |
| 3,920,603 | 11/1975 | Stayner et al. | 106/291 |

*Primary Examiner*—Delbert E. Gantz
*Assistant Examiner*—Mark Bell
*Attorney, Agent, or Firm*—Millen & White

[57] ABSTRACT

Powdery pearlescent pigment compositions comprising individual particles of a flaky pearlescent pigment coated with 1 to 50 weight percent of a solid polymer, optionally containing wetting agents, fillers, additional coloring agents, UV-absorbers or scenting agents, are produced by combining a suspension of a flaky pearlescent pigment with a solution of a polymer, possibly containing other substances, and subsequently depositing polymer on the pigment flakes. The compositions can be used as pigments in cosmetics and can be stored and shipped as dry powders without loss of properties.

8 Claims, No Drawings

POWDERY PEARLESCENT PIGMENT COMPOSITIONS

CROSS REFERENCE TO RELATED APPLICATIONS

This application is a continuation-in-part application of copending U.S. application Ser. No. 763,157, filed on Jan. 27, 1977, now U.S. Pat. No. 4,116,628.

BACKGROUND OF THE INVENTION

The invention relates to novel mechanically stable, powdery pearlescent pigment compositions and their production.

Pearlescent pigments, e.g., bismuth oxy-chloride, mica flakes coated with uncolored or colored metal oxides, natural fish scales and other pearlescent pigments are extremely thin platelets or flakes, which have low mechanical strength and a high tendency to agglomerate. When such pigment flakes are handled in dry form, i.e., as a powder, the platelets are very easily destroyed by rubbing together. The result is reduction of the pearlescence and the luminosity of the pigment.

In order to prevent this reduction in quality, valuable pearlescent pigments are made commercially available in the form of suspensions, because pigments are relatively stable in this form.

However, suspensions have several disadvantages:

(1) the nature of the dispersing agent must be coordinated with the intended use of the pigment by the purchaser;

(2) complicated systems to prevent deposition of the pigment on storage are required, but do not always operate successfully;

(3) the suspension must be packaged so that the liquid dispersing agent neither leaks away nor evaporates.

The foregoing procedures are quite expensive, aside from the fact that large amounts of dispersing agent must, of necessity, be transported, whereby the volume of material transported is unnecessarily increased. Furthermore, liquid dispersing agents are unacceptable for some uses.

Each of these difficulties could be avoided if the pigments could be handled as a dry powder, without reduction of the quality of the pigment. This has not hitherto been possible.

It is known to coat pigments with organic components to simplify the incorporation of pigments, e.g., into synthetic resins. Typical processes for the production of such pigments are described in U.S. Pat. No. 3,650,792, published German Specification Number 2,001,381 and German Patent Specification Number 1,544,830. However, in each of these cases, metal oxide pigments, usually titanium dioxide pigments, which are normally handled as powders, are used. These pigments are mechanically stable owing to a spheroidal shape. Modification of these pigments with organic components merely serves to improve dispersability of the pigments.

Pearlescent pigments have not hitherto been treated in this way. From known results, it could not have been predicted that coating the pigment flakes or platelets, which are very susceptible to breakage, with a solid polymer would provide a pearlescent pigment which can be handled in the form of powder without a noteworthy reduction of quality.

Thus, there has been a continuing need for flaky or platelike pigments which are less sensitive to mechanical stresses than those previously known, but which are not inferior to known pigments in pearlescence or luminosity.

This problem has been solved by the preparation of the pigment compositions according to this invention.

It is an object of the invention to provide powdery pearlescent pigment compositions which are resistant to a loss of properties on handling or shipping as a dry powder.

It is a further object of the invention to provide a process for the production of such powdery pearlescent pigment compositions.

A further object of the invention is the use of the powdery pearlescent pigment compositions in cosmetic formulations.

Other objects will be apparent to those skilled in the art.

SUMMARY OF THE INVENTION

In a composition aspect, this invention relates to powdery, pearlescent pigment compositions having resistance to agglomeration and the adverse effects of mechanical stresses during handling and shipment in the form of a dry powder, comprising individual particles of a flaky or plate-like pigment coated with 1-50% by weight of the coated particles of a solid polymer to form a powder essentially without pearlescence, i.e., which has lost its pearlescent or nacreous nature.

In another composition aspect, this invention relates to a process for the preparation of the novel powdery pearlescent pigment compositions, comprising the steps of (a) forming a suspension of the pigment particles in a solution of a solid polymer in a solvent therefor; and (b) removing the solid polymer from solution in the presence of the suspended pigment particles under conditions which deposit the solid polymer on the individual pigment particles, in an amount of from 1-50% by weight of the polymer-coated pigment particles, thereby coating the individual pigment particles with the solid polymer.

In another aspect, this invention relates to a method for increasing the resistance of flaky or plate-like pigment particles to agglomeration, enhancing the resistance of pigment particles to mechanical stresses and decreasing loss of pearlescence or luminosity of pigment particles during handling or shipment in the form of dry powder, comprising the steps of (a) combining a suspension of flaky or plate-like pearlescent pigment particles with a solution of a solid polymer, and (b) depositing the solid polymer on individual pigment particles and thereby coating the individual pigment particles with said solid polymer.

DETAILED DISCUSSION

Any solid polymer, except tacky or sticky polymers, is usable as a coating for the novel powdery pearlescent pigments. Typical of the large variety of usable polymers are, e.g., polyvinyl pyrrolidone; polyacrylamide; cellulose polymers, e.g., nitrocellulose, hydroxyalkylcellulose, alkylhydroxyalkylcellulose and carboxymethylcellulose; polystyrene; polyolefins, such as polyethylene and polypropylene and polycarbonates, or mixtures thereof. Water soluble polymers, especially polyvinyl pyrrolidone, are preferred. However, in principle, any polymer which is soluble in a solvent and is solid and not sticky in dry state, is suitable.

The polymers suitable for the practice of the invention have an average molecular weight of about $10^4$ to $10^6$, but these limits are not critical.

Any conventional pearlescent pigment can be used as base pigment for the new pigment compositions of the invention. Exemplary of these pigments are bismuth oxy-chloride pigments, natural fish scales (guanine), pigments based on mica flakes, e.g., mica platelets coated with titanium dioxide, zirconium dioxide, aluminum oxide, iron oxides and/or mixtures of metal oxides. Some types of pearlescent pigments contain other pigments, e.g., Berlin Blue.

Qualitatively improved powdery pearlescent pigments are obtained when the content of the polymer is as low as about 1%. Preferably, however, the range is 2 to 25%, most preferably, 3 to 15%. The percentage values are weight percent of polymer based on the total weight of the polymer-coated pigment.

A surprising aspect of this invention is that the luster (pearlescence; nacreousness) of the novel coated pigments after removal of the coating is as good as conventional lustrous (pearlescent; nacreous) pigments, i.e., is essentially the same as that of pigments prior to coating, despite the fact that the coated particles lose their luster (pearlescence; nacreousness) due to the presence of the polymeric coating. This is true even when the pigments are coated with relatively large amounts of polymer. Thus, the proportion of polymer in the pigment compositions can be about 50% and more without impairment in luster being noticeable after the work-up.

A suspension of the starting pigment in a solution of the polymer can be produced by first suspending the starting pigment in a suspending agent and then mixing the suspension with a solution of the polymer in a solvent. The requirements for the solvent and suspending agent are that the polymer is readily dissolved and the starting pigment is suspended therein without noteworthy agglomeration and that when the pigment suspension and polymer solution are combined, precipitation of the polymer does not occur. The use of the solvent for the polymer as the suspending agent for the pigment is therefore preferred.

The solvent selected in each case depends on the nature of the starting pigment and on the polymer selected for the coating. Suitable solvents can easily be found for each pair of starting pigment and polymer by simple experiments known to those skilled in the art. For suspending bismuth oxychloride flakes, halogenated hydrocarbons; lower aliphatic alcohols; esters, e.g., ethyl acetate; and ketones, e.g., acetone, are suitable. For guanine, isopropanol is especially preferred, but lower alcohols and lower esters and ketones can be used. Mica flakes coated with titanium dioxide are advantageously suspended in halogenated hydrocarbons; lower aliphatic alcohols; esters, e.g., ethyl acetate or butyl acetate; and ketones, e.g., acetone. Water is also frequently suitable as suspending agent.

The amount of starting pigment suspended in the suspension is not critical, but should not generally exceed 80% by weight, because the suspension becomes too viscous and the pigments have a greater tendency to agglomerate. On the other hand, the concentration should not be too low, because the necessary amounts of solvent become too large. For an economically feasible process, the pigment content usually is between about 25 and 80%.

The polymer dissolved in the pigment suspension is then deposited on the pigment flakes. For this purpose, numerous known methods can be employed. Deposition can take place, e.g., by addition of a precipitating agent (non-solvent) to the suspension which renders the polymer insoluble, by adding the suspension to a precipitating agent or by spray drying the suspension.

The sole requirement for the precipitating agent is that the polymer is so insoluble therein that polymer is precipitated out of solution by addition of the precipitating agent to the solvent solution or vice versa. For most polymers, aliphatic or aromatic hydrocarbons are suitable precipitating agents.

Since for each combination of starting pigment/polymer, a whole series of combinations of solvent/precipitating agent are suitable, it is expedient to select a combination capable of simple separation, e.g., by distillation, so as to simplify working up the resultant solvent mixture.

Examples of a multiplicity of possible solvent/nonsolvent combinations for application of, e.g., polyvinyl pyrrolidone polymer to pigment flakes are: chloroform/petroleum ether; chlorofrom/cyclohexane; chloroform/benzene; chloroform/toluene; chloroform/xylene; isopropanol/petroleum ether; methanol/petroleum ether and ethyl acetate/petroleum ether.

If the pigments of the invention are produced by spray drying the suspension, e.g., in a spray drying plant, then a precipitating agent is not required. The solvent or suspending agent will be selected by different criteria since, in the case of spraying, the flammability or toxicity of the solvent is of greater consequence. For these reasons, water is a very advantageous solvent, except that only water-soluble polymers, e.g., polyvinyl pyrrolidone, can be dissolved therein.

Coating of the starting pigment with polymer can also be conducted in the presence of a wetting agent, which is thereby partly taken up in the enveloping polymer layer. The presence of a wetting agent in the pigment product is advantageous because in many cases, it makes it easier for the user to incorporate the pigment into his product.

Anion- and cation-active, neutral and amphoteric wetting agents can be used. A summary of various classes of wetting agents and statements regarding a multiplicity of commercially-used wetting agents is found in Kirk-Othmer, "Encyclopedia of Chemical Technology", Interscience Publishers, New York, 1969, Vol. 19, pages 507–593, under the title reference "Surfactants". Any wetting agent disclosed therein, in principle, is suitable. Thoseskilled in the art can determine the wetting agent best suited for a particular function by simple experiments.

Preferred wetting agents include, for example, dodecylbenzenesulfonic acid triethanolamine salt, fatty acid monoethanolamides and fatty acid polyglycolesters and -diesters like stearic acid polyglycolester.

If the polymer is precipitated out of the pigment suspension, the amount of wetting agent added to the suspension is 0 to 2 weight percent by weight of the polymer plus starting pigment. In this method, the wetting agent is not completely incorporated into the pigment because some remains behind in the solvent. As a rule, the content of wetting agent in the final pigment composition is between 0 to 1%.

When the novel pigments are produced by spray drying, all of the added wetting agent remains in the final pigment. Therefore, in this method of production, a maximum of 1% of wetting agent is ordinarily employed.

In addition to wetting agents, other substances can be incorporated into the polymer layer precipitated onto the pigments. Included are substances which can be present in the compositions suitable for the end use intended for the pigment compositions, e.g., coloring agents (color pigments or dyestuffs), fillers (so-called extenders) or other substances affecting the properties of the final composition in a desired way, e.g., UV-absorbers for light protective preparations or perfumes for scenting the pigment compositions.

For incorporation in the product, the added substances can either be dissolved or suspended in the solvent. When the polymer is precipitated, the added substances are surrounded by polymer and become fixed on the surface of the pigment particles.

The amount of additional substances which can be added is not critical and depends solely on the contemplated use of the pigment composition. Perfumes are used in amounts of less than 1% by weight. Filling materials or additional color pigments, however, can be added in amounts of up to 40% by weight of the coated pigment composition. As a rule, however, such additional substances are added in a total amount of about 5 to about 30% by weight of the coated pigment composition.

If large amounts of additives are used, it is preferable to use larger amounts of polymer. About 5 to about 25% by weight of polymer is preferred.

Pearlescence and luminosity of embedded pearlescent pigments are not influenced negatively by the added substances. When the powdery pearlescent pigment compositions containing additional substances in the polymer layer are formulated into a composition suitable for use, e.g., by adding a solvent for the polymer, the additives and pearlescent pigments are liberated. Thus, the additives need not be worked into the final composition in a separate step, although this is possible, too, as they are already present in the powdery pearlescent pigment composition. Thus, ready-to-use compositions, e.g., nail enamel, can be prepared in a one-step process from the novel pigment compositions.

The spray dried product usually requires no further treatment. When, however, the polymer is precipitated out of a pigment suspension, the coated pigment is separated in the usual way, e.g., by filtration from the solvent mixture and drying.

A comminution procedure optionally follows to break up agglomerated pigment particles which have formed during the precipitation. The novel powdery pigments are remarkably stable even to such a procedure. The agglomerates, which amount to only a small fraction of the product, can also be removed by sieving. A sieving procedure is recommended after drying and optionally comminution. Very fine particles can thereby be separated out and batches with quite definite particle size can be produced. As a rule, it is sufficient to sieve the product obtained through a relatively coarse mesh sieve of about 0.35–0.5 mm mesh size.

The particle sizes of the pearlescent pigment of the invention vary within the usual limits and are, as a rule, between 1 and 150 $\mu$m. Preferred particle sizes are subject to the same selection criteria as for other pearlescent pigments. As a rule, pigments with a preponderant particle size of 10–30 $\mu$m are preferred.

The main advantage of the new, powdery pearlescent pigments is that the new pigments no longer need to be used in suspension, but can be employed as freely flowing powder. Thus, difficulties connected with the production and stabilization of the suspensions are avoided and the incorporation of the pigments into the most varied substrates is easier for the user.

The pearlescent pigments can be separated from the coating polymer with a solvent for the polymer. Advantageously, the solvent is a component of the final formulation in which the pearlescent pigment is to be used. However, a brief pre-treatment of the pearlescent pigment compositions with the corresponding solvent can also take place before addition to the final formulation.

The novel compositions can be employed, especially advantageously for pigmenting cosmetic compositions. Pearlescent pigments are employed therein, depending upon the intended use, in amounts of 0.1 to 80% by weight. The novel coated pigments can, however, be used in virtually any application in which the corresponding uncoated pearlescent pigments are used.

Cosmetic compositions in which the coated flaky pigment compositions can be used include, but are not limited to, nail enamel, lipstick, powder, suntan lotion, compact powder and liquid eyelid-shadow.

These compositions are formulated according to G. A. Nowak, Die Kosmetischen Praparate, Verlag Chemische Industrie H. Ziolkowsky, Augsburg, Western Germany, using the pigments of the invention instead of conventional pigment suspensions.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A suspension of 500 g of BiOCl pearlescent pigment, particle size 1 to 50$\mu$, in 500 g chloroform is mixed with a solution of 25 g of polyvinyl pyrrolidone, average molecular weight about $4 \times 10^4$, and 5 g of dodecylbenzenesulfonic acid triethanolamine salt in 60 g of chloroform and dropped into 2 kg of toluene. The precipitated product is separated, roughly broken up, dried at 50° C. and sieved. There is obtained 510 g of a powdery pearlescent pigment which contains about 95% BiOCl.

EXAMPLE 2

A suspension of 30 g of natural guanine in 106 g of isopropanol is mixed with a solution of 5.7 g of polyvinyl pyrrolidone, average molecular weight about $4 \times 10^4$, and 0.3 g of dodecylbenzenesulfonic acid triethanolamine salt in 25 g of isopropanol and dropped into 0.5 l of toluene. The precipitated product is separated, roughly broken up, dried at 50° C. and sieved. There is obtained 34 g of freely-flowing pearlescent pigment which contains about 84% of natural guanine.

EXAMPLE 3

40 g of mica/titanium dioxide pearlescent pigment (64% mica, 36% TiO$_2$) prepared according to the method described in U.S. Pat. No. 3,553,001, particle size 10–40$\mu$, are suspended in a solution of 5 g of polyvinyl pyrrolidone, average molecular weight about $4 \times 10^4$, in 100 g of chloroform. The suspension is dropped into 0.5 l of toluene. The precipitated product is separated off, roughly broken up, dried at 50° C. and sieved. The product is 44 g of a powdery pearlescent pigment which contains about 90% mica/titanium dioxide.

EXAMPLE 4

A suspension of 10 g of BiOCl pigment, particle size 1 to 50μ, in 10 g of chloroform is mixed with a solution of 10 g of polyvinyl pyrrolidone, average molecular weight about $4 \times 10^4$, in 100 g of chloroform and dropped into ice cold toluene at 0° C. The precipitated product is separated, roughly broken up, dried and seived. 19 g of powdery pearlescent pigment which contains about 50% BiOCl, is obtained.

EXAMPLE 5

45 g of mica/TiO$_2$ pigment (mica 59%, TiO$_2$ 41%), prepared according to the method described in U.S. Pat. No. 3,553,001, are suspended in a solution of 5 g of carboxymethyl cellulose in 100 g of water. The suspension is dropped into 500 ml of ethanol. The precipitated product is separated, dried at 50° C. and sieved. 48 g of powdery pearlescent pigment which contains about 90% mica/TiO$_2$, is obtained.

EXAMPLE 2

A suspension of 820 g of BiOCl pigment in 800 g of chloroform is mixed with a well-stirred suspensiion of 80 g carmine in a solution of 100 g of polyvinyl pyrrolidone and 10 g dodecylbenzenesulfonic acid triethanolamine salt in 300 g of chloroform. The resulting suspension is dropped with stirring into 4 kg of toluene. The precipitated product is separated, roughly broken up, dried and sieved. There is obtained 950 g of a red powdery pearlescent pigment preparation containing 82% BiOCl and 8% carmine.

EXAMPLE 7

A suspension of 580 g of BiOCl pigment in 550 g of chloroform is mixed with a well-stirred suspension of 320 g of iron oxide yellow (C yellow 8) in a solution of 100 g of polyvinyl pyrrolidone and 10 g dodecylbenzenesulfonic acid triethanolamine salt in 600 g of chloroform. The resulting suspension is dropped with stirring into 4 kg of toluene. The precipitated product is separated off, roughly broken up, dried and sieved. The product is 950 g of a yellow pearlescent pigment preparation containing 58% BiOCl and 32% color pigment.

EXAMPLE 8

Compact Powder

To 40 parts of the pigment composition of Example 6 and 52 parts of talcum is a quickly rotating mixer is added a mixture consisting of 3 parts of desalinated water, 4 parts of glycerine and 1 part of fatty acid polyglycolester. The resulting homogenous mixture is pressed into powder pans at a pressure of about 100 bar.

EXAMPLE 9

Liquid Eyelid-Shadow (a) Desalinated water: 7 parts
(b) An emulsion consisting of 12% by weight of cetyl alcohol, 8% by weight of fatty alcoholpolyglycolether, 0.25% by weight of 4-hydroxybenzoic acid methylester and 79.75% by weight of desalinated water: 15 parts
(c) The pigment composition of Example 7: 7 parts
(d) A pigment composition prepared according to Example 7, containing 75% by weight BiOCl and 15% by weight of Berlin Blue: 8 parts
(e) A 2% solution of a film-forming polysaccharide, viscosity 65 cP at 20° C.: 20 parts
(f) A 1% solution of a structure-viscous polysaccharide, viscosity 1000 cP at 60 rpm: 35 parts
(g) Polyethyleneglycol, average molecular weight 600: 8 parts The ingredients are combined under stirring in the given succession.

The formulation can additionally be scented.

The preceding examples can be repeated with similar success by substituting the generically or specifically described reactants and/or operating conditions of this invention for those used in the preceding examples.

From the foregoing description, one skilled in the art can easily ascertain the essentially characteristics of this invention, and without departing from the spirit and scope thereof, can make various changes and modifications of the invention to adapt it to various usages and conditions.

What is claimed is:

1. A dry, powdery essentially lusterless composition having resistance to agglomeration and the adverse effects of mechanical stresses during handling and shipment in the form of a dry powder, comprising individual particles of a flaky or plate-like pigment which in uncoated form are pearlescent, coated with 1-50% by weight of the coated particles of a removable coating of a solid polymer which lusterless composition, when the polymer coating is removed from the pigment particles, becomes pearlescent.

2. The composition of claim 1, wherein the solid polymer is polyvinyl pyrrolidone, polyacrylamide, nitrocellulose, alkyl cellulose, hydroxyalkyl cellulose, carboxymethyl cellulose, polystyrene, polyethylene, polypropylene, a polycarbonate, or a mixture thereof.

3. The composition of claim 2, wherein the pigment particles are coated with polyvinyl pyrrolidone.

4. The composition of claim 1, wherein the coated particles contain up to 1% by weight thereof of a wetting agent.

5. The composition of claim 1, containing up to 40% by weight thereof of an additional color pigment.

6. The composition of claim 1, wherein the pearlescent pigment particles are nacreous metal oxide-coated mica flake pigment particles.

7. The composition of claim 1, wherein the pearlescent pigment particles are nacreous bismuth oxy-chloride pigment particles.

8. The composition of claim 6, wherein the pigment particles are coated with 2-25% by weight of the coated particles of polyvinyl pyrrolidone.

* * * * *